United States Patent [19]

Degen et al.

[11] Patent Number: 4,707,266

[45] Date of Patent: Nov. 17, 1987

[54] POLYAMIDE MEMBRANE WITH CONTROLLED SURFACE PROPERTIES

[75] Inventors: Peter J. Degen; Irving B. Joffee, both of Huntington; Thomas C. Gsell, Levittown, all of N.Y.

[73] Assignee: Pall Corporation, Glen Cove, N.Y.

[21] Appl. No.: 850,061

[22] Filed: Apr. 7, 1986

Related U.S. Application Data

[63] Continuation of Ser. No. 459,956, Jan. 21, 1983, abandoned, which is a continuation-in-part of Ser. No. 346,118, Feb. 5, 1982, abandoned.

[51] Int. Cl.$^4$ .............................................. B01D 13/00
[52] U.S. Cl. .................................. 210/638; 210/651; 210/500.38; 521/27
[58] Field of Search ............. 521/27; 210/638, 500.34, 210/500.42, 500.38, 500.35, 500.36, 651, 654; 427/244, 245

[56] References Cited

U.S. PATENT DOCUMENTS

| | | | |
|---|---|---|---|
| 2,783,894 | 4/1957 | Lovell et al. | 264/41 |
| 2,884,387 | 4/1959 | Bieber et al. | 264/41 |
| 2,926,154 | 2/1960 | Keim | 210/23 R |
| 3,100,721 | 12/1963 | Holden | 264/41 |
| 3,208,875 | 9/1965 | Holden | 264/41 |
| 3,224,986 | 12/1965 | Butler et al. | 264/41 |
| 3,225,107 | 12/1965 | Kirkland et al. | 260/652 |
| 3,408,315 | 10/1968 | Paine | 264/41 |
| 3,497,451 | 2/1970 | Hoehn et al. | 210/500 M X |
| 3,510,417 | 5/1970 | Mizutani et al. | 204/130 |
| 3,522,335 | 7/1970 | Rowley | 210/500 M X |
| 3,524,546 | 8/1970 | Hoehn et al. | 210/23 |
| 3,556,305 | 1/1971 | Shorr | 210/490 |
| 3,567,630 | 3/1971 | Lukach | 210/23 R |
| 3,567,631 | 3/1971 | Lukach et al. | 210/23 R |
| 3,615,024 | 10/1971 | Michaels | 210/500 M X |
| 3,737,045 | 6/1973 | Hashimoto et al. | 210/500 M X |
| 3,746,668 | 7/1973 | Hiratsuka et al. | 264/41 |
| 3,772,223 | 11/1973 | Broutelles et al. | 264/41 |
| 3,808,305 | 4/1974 | Gregor | 264/330 |
| 3,852,224 | 12/1974 | Bridgeford | 210/23 R X |
| 3,876,738 | 4/1975 | Marinaccio et al. | 210/23 H X |
| 3,901,810 | 7/1975 | Brooks et al. | 210/500 M X |
| 3,950,247 | 4/1976 | Chiang et al. | 210/640 X |
| 3,951,815 | 4/1976 | Wrasidlo | 210/500 M X |
| 3,957,651 | 5/1976 | Kesting | 210/500.2 X |
| 3,980,605 | 9/1976 | Steigelmann et al. | 210/500 M X |
| 4,005,012 | 1/1977 | Wrasidlo | 210/500 M X |
| 4,032,309 | 6/1977 | Salemme | 210/23 R |
| 4,039,440 | 7/1977 | Cadotte | 210/500 M X |
| 4,046,843 | 9/1977 | Sano et al. | 210/500.2 X |
| 4,047,908 | 9/1977 | Steigelmann et al. | 55/158 |
| 4,073,733 | 2/1978 | Yamauchi et al. | 210/500 M X |
| 4,106,920 | 8/1978 | Hughes et al. | 210/500 M X |
| 4,107,098 | 8/1978 | Tamura et al. | 210/23 R |
| 4,111,859 | 9/1978 | Strop et al. | 210/23 H |
| 4,147,622 | 4/1979 | Nussbaumer | 55/16 |
| 4,188,354 | 2/1980 | Munari et al. | 210/500 M X |
| 4,203,847 | 6/1980 | Grandine | 210/500 M |
| 4,208,455 | 6/1980 | Giuffre et al. | 210/23 R |
| 4,244,817 | 1/1981 | Yaginuma | 210/500 M X |
| 4,250,029 | 2/1981 | Kiser et al. | 210/500 M X |
| 4,253,963 | 3/1981 | Franken et al. | 264/41 |
| 4,265,745 | 5/1981 | Kawaguchi et al. | 210/500 M X |
| 4,330,406 | 5/1982 | Sano et al. | 210/500 M X |
| 4,340,479 | 7/1982 | Pall | 210/493.2 X |
| 4,340,480 | 7/1982 | Pall et al. | 210/500 M X |
| 4,377,481 | 3/1983 | Jakabhazy | 210/500 M |
| 4,387,024 | 6/1983 | Kurihara et al. | 210/500 M X |
| 4,388,189 | 6/1983 | Kawaguchi et al. | 210/500 M X |
| 4,412,922 | 11/1983 | Mir | 210/500.2 X |
| 4,432,875 | 2/1984 | Wrasidlo et al. | 210/500.2 |
| 4,604,208 | 8/1986 | Chu et al. | 210/636 |

FOREIGN PATENT DOCUMENTS

| | | | |
|---|---|---|---|
| 0031730 | 6/1981 | European Pat. Off. | 210/23 R |
| 0050864 | 5/1982 | European Pat. Off. | 210/500 M X |
| 0056175 | 7/1982 | European Pat. Off. | 210/23 H |
| 0066814 | 12/1982 | European Pat. Off. | 210/500 M |
| 0099699 | 2/1984 | European Pat. Off. | 210/500 M |
| 2457355 | 5/1975 | Fed. Rep. of Germany | 210/500 M |
| 2622805 | 1/1977 | Fed. Rep. of Germany | 210/500 M |
| 2452310 | 10/1980 | France | 210/500 M |
| 401668 | 1/1960 | Japan | 210/500 M |
| 478906 | 7/1968 | Japan | 210/500 M |

(List continued on next page.)

OTHER PUBLICATIONS

European Search Report, EP 83 30 0517.

Primary Examiner—Frank Spear
Attorney, Agent, or Firm—Leydig, Voit & Mayer

[57] ABSTRACT

Surface modified, skinless, hydrophilic, microporous, polyamide membranes with controlled surface properties are prepared by the steps of preparing a casting solution comprised of (A) a casting resin system comprised of (a) an alcohol-insoluble polyamide resin, and (b) a water-soluble membrane surface modifying polymer having functional polar groups and a molecular weight of 10,000 or greater, and (B) a solvent system in which the casting resin system is soluble; inducing nucleation of the casting solution by controlled addition of a nonsolvent for the casting resin system under controlled conditions to obtain a visible precipitate of casting resin system particles, thereby forming a casting composition; spreading the casting composition on a substrate to form a thin film; contacting and diluting the film of the casting composition with a liquid nonsolvent system for the casting resin system, thereby precipitating the casting resin system from the casting composition in the form of a thin, skinless, hydrophilic, surface modified, microporous, polyamide membrane; and washing and drying the membrane. The membranes of this invention are characterized by having fine pore ratings, the surface properties thereof being substantially controlled by functional polar groups of a membrane surface modifying polymer and having the capability, through the functional polar groups of the modifying polymer, of reacting or interacting with particulates and/or nonparticulates in a fluid.

65 Claims, No Drawings

FOREIGN PATENT DOCUMENTS

| | | | | | | | | |
|---|---|---|---|---|---|---|---|---|
| 51-79684 | 3/1976 | Japan | 210/500 M | 55-8887 | 7/1980 | Japan | 210/23 R |
| 4737870 | 5/1976 | Japan | 210/500 M | 55-129124 | 9/1980 | Japan | 210/23 R |
| 53-134871 | 2/1978 | Japan | 210/23 R | 1195823 | 6/1970 | United Kingdom | 210/500 M |
| 53-92485 | 3/1978 | Japan | 210/23 R | 1210051 | 10/1970 | United Kingdom | 210/500 M |
| 53-60883 | 6/1978 | Japan | 210/23 H | 1302619 | 1/1973 | United Kingdom | 210/23 H |
| 55-24928 | 2/1980 | Japan | 210/23 H | 1411843 | 10/1975 | United Kingdom | 210/23 H |
| 55-66935 | 5/1980 | Japan | 210/23 H | 1499134 | 1/1978 | United Kingdom | 210/23 H |
| 55-69627 | 6/1980 | Japan | 210/23 H | 1602085 | 11/1981 | United Kingdom | 210/500 M |

POLYAMIDE MEMBRANE WITH CONTROLLED SURFACE PROPERTIES

This application is a continuation of application Ser. No. 459,956 filed Jan. 21, 1983 which is a continuation-in-part of application Ser. No. 346,118 filed Feb. 5, 1982, both now abandoned.

TECHNICAL FIELD

The present invention relates to microporous membranes, their preparation and their use. More particularly, the invention relates to novel microporous polymeric membranes which combine the properties of particle removal through mechanical filtration with the ability to interact in a controlled fashion with selected components of the fluid being filtered.

Microporous membranes have been recognized for some time as useful for filtering fine particles from gas and liquid media. U.S. Pat. No. 4,340,479 discloses a process for manufacturing microporous polyamide membranes with certain desirable filtration characteristics. Membranes prepared by the process disclosed in U.S. Pat. No. 4,340,379 are hydrophilic, have narrow pore size distributions and pore ratings as fine as about 0.04 micrometer. For many filtering requirements, those membranes perform very effectively.

The function of a filter is the removal of suspended particulate material and the passage of the clarified fluid medium. A filter membrane can achieve fluid clarification by different mechanisms. Particulate material can be removed through mechanical sieving wherein all particles larger than the pore diameter of the filter membrane are removed from the fluid. A filter may also remove suspended particulate material by adsorption onto the filter membrane surfaces. Removal of particulate material by this mechanism is controlled by the surface characteristics of (1) the suspended particulate material and (2) the filter membrane.

Colloid stability theory can be used to predict the interactions of electrostatically charged particles and surfaces. If the charges of suspended particles and the filter membrane surface are of like sign and with zeta potentials of greater than about 20 mV, mutual repulsive forces will be sufficiently strong to prevent capture by adsorption. If the zeta potentials of the suspended particles and the filter membrane surface are small, or of opposite sign, particles will tend to adhere to the filter membrane surfaces. By careful control of the zeta potential of the filter material, selective particulate removal can be achieved.

There are many industrial processes in which it is desired to remove larger particles from suspensions of costly smaller particles, e.g., catalysts and colloidal drugs. In such applications, it is extremely undesirable if the filter intended to act as a sieve for the larger particles removes a portion of the costly smaller particles fraction by adsorption. There are also applications, such as the filtration of beverages, where flavor components and/or dyes are present in colloidal form. In these cases, too, removal of these components by adsorption onto the filter membrane is undesirable. Because most suspensions of particles encountered in industrial practice have a negative zeta potential, such unwanted adsorptive removal can be minimized if a negative charge can be imparted to the filtering medium.

The unusual zeta potential versus pH profile of the hydrophilic polyamide membranes of U.S. Pat. No. 4,340,479 is believed to result from the positioning of a high concentration of the amine and carboxylic acid end groups of the polyamide at the exposed surfaces of the membrane. That profile, strongly negative at pHs above 6.5, approaches zero and then becomes positive in acidic media. Accordingly, the membranes of U.S. Pat. No. 4,340,479 have the ability to remove small negatively charged particles in acidic media by adsorption. Conversely, these membranes have limited capability to remove positively charged particles in acidic media.

By modifying the surface characteristics of the hydrophilic membranes disclosed in U.S. Pat. No. 4,340,479 to, for instance, provide a negative zeta potential over the acidic range, the spectrum of uses for these materials in filtration would be substantially expanded.

In addition to purification by particle removal, certain of the modified membranes of this invention can simultaneously purify liquids by removal of dissolved metallic contaminants through complex formation by interaction with the metal species. The mechanisms by which this occurs are varied. Removal may occur by an ion exchange mechanism wherein a membrane modified to have a predominance of anionic groups at the membrane surfaces may behave as a cation exchange resin and trap the dissolved metal species, most of which are present as cations in aqueous solution.

Alternatively, dissolved metals may be removed from solution by a mechanism wherein the metal is bound as a stable complex or coordination compound with chemical functional groups present at the surfaces of the modified membrane. This mechanism is very useful in the removal or recovery of zero-valent metal complexes, such as those used as industrial catalysts and of negatively charged complexes, such as those found in plating baths. These two types of complexes, in which costly metals are frequently found, are not removed from solution by a cation-exchanging material.

Thus, by modifying the surface characteristics of the hydrophilic membranes disclosed in U.S. Pat. No. 4,340,479 to, for instance, provide a surface with which dissolved metals would be able to react chemically, the spectrum of uses for these materials in filtration would be further expanded.

The existence of interactions between certain biological materials and other natural or synthetic materials is also well known to those skilled in the art. These interactions are used routinely in the purification of biological and biochemical preparations. One example of this is the widespread technique of affinity chromatography which is described in "Theory and Practice in Affinity Chromatography", P. V. Sundaram and F. Eckstein, Academic Press, New York, 1978. In affinity chromatography, convenient physical supports are chemically modified with substances with which various biological materials have a strong positive interaction. The use of these modified supports in a chromatographic process has enabled the separation of complex biochemical mixtures into their components. Materials which have been isolated in this manner include proteins, pyrogens and immune factors, all of which are useful products to the pharmaceutical and biological industries. Commercial purification of such materials by means of affinity chromatography would be a very expensive operation. However, by modifying the surface characteristics of the hydrophilic membranes disclosed in U.S. Pat. No. 4,340,479 to, for instance, enable chemical modification of the membrane and thereby provide a strong affinity between certain biological materials and the membrane, the cost of such purification could be substantially reduced and the spectrum of uses of these membranes in filtration processes would again be substantially expanded.

Another technical area in which the membranes of this invention can be used is in the immobilization of enzymes. Enzymes can be chemically bound to many solid surfaces by a variety of methods known to those skilled in the art. Such methods are described in "The Proteins", J. Porath and T. Kristiansen, H. Neurath, Editor in 3rd Edition, Academic Press, 1975. Immobilized enzymes on various solid supports are presently being used in industrial operations, including food processing and preparation of pharmaceuticals. As biotechnology progresses it is expected that the use of immobilized enzymes will become even more widespread. The surface modified, microporous membranes of this invention, when used as supports for immobilized enzymes, serve not only as a means for exposing the enzyme to a substrate, but also as a convenient means of separating the enzyme from the product, as well as a means for the simultaneous removal of unwanted particulate contaminants, such as cell debris, which is a frequent by-product in commercial enzyme preparations.

The present invention is directed, then, to surface modified, microporous, hydrophilic polyamide membranes, their preparation and use. The process of this invention provides microporous membranes with fine pore ratings and narrow pore size distributions. The surface modified membranes of this invention have pore surfaces bearing selected functional polar groups, providing unique and highly desirable properties enabling them to react or interact in a controlled manner with particulate matter in a fluid, non-particulate matter in a fluid, or both. This controlled reaction or interaction between the membrane and one or more of the components of the fluid make the filter membranes of this invention useful in the purification of beverages, chemical process streams, and waste streams. They also can be chemically modified after formation as required for use in pharmaceutical and biological preparations.

DISCLOSURE OF INVENTION

The subject invention is directed to surface modified, hydrophilic, microporous polyamide membranes with controlled pore surface properties, capable of reacting or interacting with (a) particulate matter in a fluid, (b) non-particulate matter in a fluid, or (c) both (a) and (b), and a process for preparing these membranes by the steps of (1) preparing a casting solution comprised of (A) a casting resin system comprised of (a) an alcohol-insoluble polyamide resin having a ratio $CH_2:NHCO$ of methylene $CH_2$ to amide $NHCO$ groups within the range from about 5:1 to about 7:1 and (b) a water-soluble, membrane surface modifying polymer having functional polar groups and a molecular weight of 10,000 or greater; and (B) a solvent system in which the casting resin system is soluble; (2) inducing nucleation of the casting solution by controlled addition of a nonsolvent for the casting resin system under controlled conditions of concentration, temperature, addition rate and degree of agitation to obtain a visible precipitate of casting resin system particles which may or may not thereafter partially or completely redissolve, thereby forming a casting composition; (3) preferably filtering the casting composition to remove visible precipitated particles; (4) spreading the casting composition on a substrate to form a thin film thereof on the substrate; (5) contacting and diluting the film of casting composition with a liquid nonsolvent system comprised of a mixture of solvent and nonsolvent liquids and containing a substantial proportion of the solvent liquid but less than the proportion in the casting composition, thereby precipitating the casting resin system from the casting composition in the form of a thin, skinless, hydrophilic, surface modified, microporous membrane; (6) washing the membrane to remove solvent; and (7) drying the membrane.

The surface modified, alcohol-insoluble polyamide membranes of this invention have the unusual property of being hydrophilic, i.e., they are readily wetted by water, typically being wetted through in 3 seconds or less, preferably 1 second or less, when immersed in water (see U.S. Pat. No. 4,340,479), have pore sizes (also referred to as pore ratings or pore diameters) of from about 0.04 to about 10 micrometers or more, preferably 0.1 to 5 micrometers, have, in certain instances, modified zeta potentials, e.g., negative zeta potentials in acidic media, have filtration efficiencies ranging from molecular dimensions (pyrogens) to particulates larger than the pore sizes and, accordingly, are highly desirable as filter media, particularly for producing bacterially sterile filtrates. The membranes of this invention have controlled pore surface properties and are capable of reacting or interacting selectively with (a) particulate material in a fluid, (b) non-particulate material in a fluid, or (c) both (a) and (b). As a result of the ability to control the surface properties of the membranes of this invention, they are also useful to remove undesired dissolved material or concentrate desired dissolved material and serve as supports for the immobilization of enzymes and in processing biological and biochemical preparations.

The membrane surface modifying polymers or resins useful in preparing the membranes of this invention are water-soluble polymers capable of reacting or interacting with (a) particulate matter in a fluid, (b) non-particulate matter in a fluid, or (c) both (a) and (b). They have molecular weights of 10,000 or greater, preferably 20,000 or greater. Preferred surface modifying polymers within this class are the polyethyleneimines, poly(-vinyl alcohol), carboxyl-containing compositions, such as polymers of acrylic acid, and sulfonic-containing compositions, such as a homopolymer of styrene sulfonic acid.

BEST MODE FOR CARRYING OUT THE INVENTION

The subject invention is directed to surface modified, hydrophilic, microporous, polyamide membranes with controlled pore surface properties, capable of reacting or interacting with (a) particulate matter in fluid, (b) non-particulate matter in fluid, or (c) both (a) and (b), and a process for preparing these membranes by the steps of (1) preparing a casting solution comprised of (A) a resin casting system comprised of (a) an alcohol-insoluble polyamide resin having a ratio of $CH_2NHCO$ of methylene $CH_2$ to amide $NHCO$ groups within the range of from about 5:1 to about 7:1 and (b) a membrane surface modifying polymer having functional polar groups and a molecular weight of 10,000 or greater; and (B) a solvent system in which the casting resin system is soluble; (2) inducing nucleation of the casting solution by controlled addition of a nonsolvent for the casting resin system under controlled conditions of concentration, temperature, addition rate and degree of agitation to obtain a visible precipitate of casting resin system particles which may or may not thereafter partially or completely redissolve, thereby forming a casting composition; (3) preferably filtering the casting composition to remove visible precipitated particles; (4) spreading the casting composition on a substrate to form a thin film thereof on the substrate; (5) contacting and diluting the film of casting composition with a liquid nonsolvent system comprised of a mixture of solvent and nonsolvent liquids and containing a substantial proportion of the solvent liquid but less than the proportion in the casting solution, thereby precipitating the casting resin system from the casting composition in the form of a thin, skinless, hydrophilic, surface modified, microporous membrane; (6) washing the membrane to remove solvent; and (7) drying the membrane.

As previously discussed, the preparation of hydrophilic, microporous, polyamide filter membranes is the subject of U.S. Pat. No. 4,340,479, the disclosure of which is incorporated herein by reference.

The hydrophilic polyamide membranes disclosed in U.S. Pat. No. 4,340,479 are prepared from alcohol-insoluble polyamide resins having a methylene to amide ratio in the range of about 5:1 to about 7:1, as are the surface modified membranes of this invention. Members of this group include copolymers of hexamethylene diamine and adipic acid (nylon 66), copolymers of hexamethylene diamine and sebacic acid (nylon 610) and homopolymers of poly-e-caprolactam (nylon 6). The preferred member in this invention is nylon 66.

In the process for manufacturing the membranes of U.S. Pat. No. 4,340,479, the polyamide resin is dissolved in a solvent, such as formic acid, and a nonsolvent, such as water, is added under controlled conditions of agitation to achieve nucleation of the solution.

In inducing nucleation of the polyamide solution, a visible precipitate is formed. This precipitate may partially or completely redissolve. Preferably, any visible particles which do not redissolve should be filtered out of the system, e.g., with a 10 micrometer filter, prior to casting the nucleated solution or casting composition.

The nucleated solution or casting composition is then cast onto a substrate, e.g., a porous polyester sheet or web or a non-porous polyester sheet, in the form of a film and this film of solution is then contacted with and diluted by a liquid nonsolvent system which is a mixture of solvent and a nonsolvent for the polyamide resin. A preferred nonsolvent liquid system for both the subject invention and that of U.S. Pat. No. 4,340,479 is a solution of water and formic acid. For this invention, the formic acid is preferably present in an amount of from about 35% to about 60% by weight, all parts and percentages herein by weight unless otherwise indicated. The polyamide resin thereupon precipitates from the solution, forming a hydrophilic membrane sheet on the substrate which can be washed to remove the solvent liquid. The membrane can then be stripped from the substrate and dried or, if the substrate is porous, it can be incorporated in the membrane to serve as a permanent support, in which event it is dried with the membrane. If the substrate is to be incorporated into the membrane, it should be porous and capable of being wetted and impregnated by the casting composition, e.g., a porous, fibrous polyester sheet with an open structure. By appropriate control of process variables, membranes with through pores of uniform size and shape can be obtained. Conversely, if desired, tapered through pores, wider at one surface of the sheet and narrowing as they proceed towards the opposite surface of the sheet, can be obtained.

The same general procedure described above is followed in manufacturing the surface modified membranes of this invention except that the membrane surface modifying polymers used in the subject invention are combined with the polyamide resin and the resulting modifying polymer/polyamide casting solution after nucleation to form the casting composition, is cocast, resulting in unique membranes with novel properties extending the range of uses for microporous polyamide membranes.

The novel properties of the filter membranes prepared by the process of U.S. Pat. No. 4,340,479 are believed to result in part from the high concentration on the exposed membrane surfaces of amine and carboxylic acid end groups of the polyamide. These amine and carboxylic acid functions on the membrane surfaces result in unexpected membrane properties, such as their unusual zeta potential versus pH profile and their hydrophilic character.

As previously stated, it has now been discovered that the surface modified membranes of this invention having unexpected and novel properties can be prepared using the general procedure disclosed in U.S. Pat. No. 4,340,479 but with the addition of low levels of selected membrane surface modifying polymers to the polyamide membrane casting solutions. Thus, surface modified, hydrophilic, microporous membranes with pore surfaces having a wide variety of desirable chemical and physical chemical properties are readily and economically prepared by the cocasting process of the present invention. These desirable membrane surface properties include, for example, negative zeta potential over a wide pH range. Such membranes have use in the enhanced filtration of positively charged particulates, such as asbestos particles, through electrostatic capture. Useful surface modifying polymers for this purpose are polymers containing substantial proportions of acidic, ionizeable functional polar groups, such as carboxyl, sulfonic, phenolic and phosphoryl. These functional groups on the modified membrane surfaces provide negative zeta potential over a wide pH range, including acid media with pHs as low as 3, and enhanced filtration efficiency for positively charged particulates through electrostatic capture. Moreover, such surface modified membranes are also expected to show a reduced tendency for the adsorption of certain desirable components in pharmaceutical preparations.

Membranes prepared with selected surface modifying polymers have the ability to remove, selectively or universally, toxic and/or precious metals from aqueous fluids. Surface modifying polymers containing functional polar groups which undergo complex formation by interaction with metallic species by either ionic interaction or through complex forming interactions will produce bound metal species on the modified membrane surface. A variety of chemical functional groups are known to form stable metal complexes or metal salts and are therefore preferred functional membranes. These include amine, pyridyl, sulfonic, sulfhydryl, thiocarbonyl, phosphine, phosphoryl and imine, which are preferred because of their tendency to form stable complexes on salts with various metal species.

Membranes of the subject invention having the ability to be further chemically modified for various purposes are those which have been prepared with surface modifying polymers bearing functional groups known to undergo further reactions efficiently and under relatively mild conditions. Preferred functional groups in this class include hydroxyl, carboxyl and amine. These groups, when occupying the surfaces of the membrane, can be further chemically reacted with, for example, enzymes, and serve as an efficient substrate for the immobilization of enzymes and other materials of interest.

Addition of as little as 1 weight percent (based on the polyamide resin) of the membrane surface modifying polymer to the membrane casting solution has been found to produce microporous hydrophilic membranes whose surface properties are substantially controlled by the surface modifying polymer. It is the ability of relatively small amounts of the membrane surface modifying polymer to control the surface properties of the membrane of the present invention which is believed to provide the desirable filtration characteristics and the desirable physiochemical surface behavior of these membranes. The highly desirable properties of the membranes of the subject invention are believed to result from the unique method of preparation in which the modifying polymer becomes an integral part of the overall structure of the membrane. As noted above, these desirable characteristics are obtained and controlled with a surprisingly low proportion of the membrane surface modifying polymer.

Membrane Surface Modifying Polymers

The membrane surface modifying polymers or resins (sometimes hereinafter "modifying polymer(s)") useful in the process of this invention are those water-soluble polymers bearing the desired chemical functional groups and which are compatible with the polyamide membrane and soluble in the membrane casting solution. The preferred modifying polymers useful in the present invention are those commercially available polymers which provide a high density of the desired functional group. The greater the number of desired functional groups per weight of modifying polymer, the greater is the extent to which the modifying polymer can impart the desired surface properties to the membrane.

Functional groups useful in membranes of this invention include hydroxyl, carboxyl, sulfonic, phenolic, amine, sulfhydryl, sulfide, thiocarbonyl, phosphine, phosphoryl, thiophosphoryl, or a non-reacting (with each other) combination of any of the above groups. These functional groups are useful because (1) they are polar, (2) they have a high dipole moment, (3) they can participate in hydrogen bonding, either as donors, acceptors, or both, with materials of interest in the fluid medium, and (4) they can react in a conventional chemical sense and/or interact selectively with particulate material or dissolved material, or both, in the fluid medium. Because of their polarity and hydrogen bonding capability, these groups can interact strongly with the amine and carboxylic acid end groups of the polyamide from which the membrane is formed. While it is believed that this interaction occurs throughout the membrane structure, the nature of the membrane forming process is believed to cause preferential orientation of the modifying polymer toward the surfaces of the formed membrane. By this is meant that, as a result of the cocasting process of this invention, the modifying polymer determines the surface characteristics of the membrane. It is also believed that the interaction of the functional groups on the modifying polymer with the end groups of the polyamide results in intimate bonding of the modifying polymer and the polyamide resin forming an integral structure, thereby providing increased homogeneity of the pore surfaces of the membrane, and increased general stability, as evidenced by low levels of extractable matter, of the membranes produced by the process of this invention.

The modifying polymers used in this invention have relatively high molecular weights. In principal, strong interaction between the modifying polymer and the polyamide resin would suggest that the stability of the membrane should be increased by inclusion of a modifying polymer. Surprisingly, it has been found that the inclusion of polymers of molecular weight less than 10,000 actually tend to produce membranes having unstable surface properties. For this reason, the modifying polymers of this invention have molecular weights of 10,000 or greater. Modifying polymers of molecular weight of 20,000 or greater tend to produce stable membranes and are preferred. A particularly preferred molecular weight range is from about 25,000 to about 150,000.

Surprisingly, the low added levels of modifying polymers appear to be preferentially orientated in such a manner as to result in membranes whose surface characteristics are substantially controlled by the membrane surface modifying polymer. This result is believed to reflect both the unique membrane forming process and the hydrophilic nature of the modifying polymers. The combination of their hydrophilicity, their apparent strong interaction with the polyamide end groups and the unique membrane cocasting process is believed to result in the preferential orientation of the modifying polymers toward the membrane surface.

An additional unexpected and highly desirable characteristic of the membranes of this invention is that, while the surface modifying polymers of this invention are readily water soluble, they are not leached out of the casting composition into the nonsolvent liquid, typically water, which is used to precipitate the casting resin system. Apparently, the strong interaction of the modifying polymer with the polyamide end groups, coupled with the preferential orientation of the modifying polymer toward the membrane surface, perhaps under the influence of the nonsolvent, combine to provide a membrane whose surface properties are substantially controlled by the functional polar groups of the modifying polymer. At any rate, the unexpected result is highly desirable, providing a membrane with unique characteristics which can be prepared by an efficient and economic process.

The modifying polymer of choice depends on the type of chemical function desired at the surface of the membrane. This in turn, of course, depends upon the desired use of the membrane.

Membranes with negative zeta potentials in the acidic pH range are made with highly anionic surface modifying polymers, such as those bearing a high concentration of carboxyl (COOH) or sulfonic ($SO_3H$) groups. Examples of materials containing such functional groups are poly(acrylic acid), poly(methacrylic acid), poly(styrene sulfonic acid) and copolymers of unsaturated carboxyl and sulfonic acids with nonionic unsaturated monomers such as vinyl esters, acrylic esters, olefins and styrene.

Commercially available carboxyl-containing compositions are exemplified by the Carbopol ® series of resins (B. F. Goodrich) described as high molecular weight polymers of acrylic acid. Copolymers containing carboxylic acids are exemplified by Gantrez ® S-97, a fully hydrolyzed copolymer of maleic anhydride with methyl vinyl ether and having a molecular weight of about 67,000. Product #19205-8 (Aldrich Chemical Company) is a commercially available poly(acrylic acid) having a molecular weight of about 90,000. An example of a commercially available sulfonic acid-containing polymer is Poly Sodium Vinyl Sulfonate (Air Products and Chemicals). A preferred modifying polymer for this invention is Versa ® TL-71 (National Starch), believed to be a homopolymer of styrene sulfonic acid having a molecular weight of about 70,000.

Membranes with amine functional groups may be prepared using modifying polymers bearing amino groups which are (1) pendent from the polymer backbone, (2) form part of the polymer backbone or (3) a combination thereof. In principal, any polymer containing amino groups may be used, such as polymers containing amino styrene or amino alkyl acrylates. Condensation products of alkylene dichlorides with alkylene diamines or ammonia, such as are sometimes used as flocculating agents, may also be useful, provided they have the desired molecular weight, solubility, and compatibility set forth earlier. Preferred are such materials as the polyethyleneimines, as exemplified by the Cor-Cat ® resins (Cordova Chemical Company), which are homopolymers of aziridine with molecular weights of 30,000 and greater, Cor-Cat ® P-145 being a particularly desirable example and having a molecular weight of 50,000 to 60,000.

Membranes with hydroxyl groups may be prepared using modifying polymers containing hydroxyl groups. In principle, any polymer of high molecular weight with hydroxyl groups pendent from the polymer backbone can be used, such as polymers containing hydroxyaryl acrylates or hydroxyalkyl acrylates. However, poly(vinyl alcohol) is preferred because of its high density of hydroxyl groups. This polymer is commercially prepared by hydrolysis of poly(vinyl acetate) and is available as products having different degrees of hydrolysis, ranging from nearly 100 percent hydrolyzed to about 60 percent hydrolyzed. Particularly preferred are compositions such as Vinol ® 165 (Air Products and Chemicals), a 99.6% hydrolyzed product of molecular weight of about 110,000.

Process Conditions

The preparation of the surface modified, skinless, hydrophilic, microporous, alcohol-insoluble polyamide membranes of this invention is carried out under controlled conditions including controlled addition of the nonsolvent, e.g., water, to a solution of the polyamide and the membrane surface modifying polymer (casting solution), control of the concentration of the constituents, control of the temperature and control of the agitation of the system to induce the proper level of nucleation.

U.S. Pat. No. 4,340,479, as discussed above, has been incorporated herein by reference. The detailed discussion therein concerning the relationship of the parameters set out above is generally applicable herein and will not be repeated. Rather, a summary of the operative ranges and their relationship will be provided.

Controlled Addition Of The Nonsolvent

The manner and rate of addition of the nonsolvent to induce nucleation is interrelated with other process variables, such as intensity of mixing, temperature and the concentration of the various components of the casting solution. The term "casting solution" is used here to mean the solution made up of (A) the casting resin system and (B) the solvent system. Addition of the nonsolvent is conveniently carried out through an orifice at a rate sufficient to produce a visible precipitate which, preferably, at least in part subsequently redissolves. Maintaining all other parameters constant, casting compositions with quite different characteristics in terms of pore sizes of the resulting membranes will be obtained by varying the diameter of the orifice. The required degree of nucleation resulting from nonsolvent addition rate and orifice configuration is therefore best established by trial and error for each given system.

The controlled addition of nonsolvent is discussed in detail in U.S. Pat. No. 4,340,479. Prior to addition of the nonsolvent to induce nucleation, the casting solution is prepared. It is comprised of (A) a casting resin system comprised of (a) an alcohol-insoluble polyamide resin as described above and (b) a membrane surface modifying polymer or resin and (B) a solvent system. The solvent system may simply be a solvent for the casting resin system, e.g., formic acid. Alternatively, the solvent system may contain an amount of a nonsolvent, e.g., water. The amount of nonsolvent present in the casting solution will always be less than the amount necessary to effect the stability of the solution.

Prior to casting, nucleation of the casting solution is initiated by the controlled addition of nonsolvent liquid and agitation. The amount and rate of addition of nonsolvent liquid is controlled along with the intensity of mixing or agitation. The advantage of including nonsolvent as part of the solvent system in making up the casting solution, particularly in a continuous process, is that better control of the addition of nonsolvent can be maintained during the inducement of nucleation because smaller amounts of nonsolvent are needed due to the nonsolvent already present in the casting solution. As a result, better control of the addition rate can be maintained and a more uniform product of any desired pore size can be obtained.

Concentration Of The Constituents

All parts and percentages herein are by weight unless otherwise noted.

The casting resin system of this invention is comprised of (a) an alcohol-insoluble polyamide resin having a methylene to amide ratio of from about 5:1 to about 7:1 and (b) a surface modifying polymer or resin as previously described.

The proportion of membrane surface modifying polymer to polyamide resin in the casting solution formed as the first step in the process of this invention, based on the polyamide resin, can vary from as much as about 20 weight percent to as little as about 1.0 weight percent, that is, 20 parts of modifying polymer to 100 parts polyamide resin to 1 part of modifying polymer to 100 parts polyamide resin. The generally preferred range of added modifying polymer is from about 5 weight percent to about 15 weight percent, based on the weight of the polyamide resin. For the purpose of membrane efficiency and production economy, the addition of about 5 weight percent of the modifying polymer, based on the polyamide resin, is particularly preferred. The polyamide resin is preferably present in the casting solution in an amount of from about 10% to 20%, and the surface modifying polymer will be present then in an amount of from about 0.5% to 3%, (based on all components present in the solution).

The amount of solvent present in the casting solution formed as the first step in the process of this invention will vary dependent upon the polyamide resin and the modifying polymer used. In general, the amount of solvent present will range from about 60 to 80% (based on all components present in the solution).

It should be understood that the casting solution comprises both (1) the casting resin system, i.e., the polyamide resin and the modifying polymer or resin, and (2) the solvent system, i.e., a solvent for the polyamide resin/modifying polymer casting resin system (such as formic acid) and, if desired, a minor amount of a nonsolvent for the casting resin system (such as water).

The amount of nonsolvent, if any, present in the casting solution will in all cases be less than the amount in the liquid nonsolvent system (membrane forming bath) used to precipitate the casting resin system from the casting composition, the casting composition being the composition formed from the initially prepared casting solution by inducing nucleation in that solution and, preferably, removing visible particles from the resulting composition. Generally, when the nonsolvent is water, it will be present in the casting solution in an amount ranging from zero up to about 30% by weight, lesser amounts, such as 5–15%, being more desirable than the larger amounts (again based on all the components present in the solution.

Control Of The Temperature

The temperature of the casting solution is not critical so long as it is maintained at a constant value. Generally, however, a decrease in casting solution temperature produces a higher degree of nucleation.

Control Of The Agitation

The intensity of mixing in a given system is a function of a large number of interrelated variables. For any given system, the mixing intensity can be expressed in terms of the rotation rate of the agitator. Such equipment has many forms and designs commonly used in the mixing art and is difficult to quantify. Thus, trial and error experimentation involving customary variables is necessary to establish the operable range of mixing intensities suitable for a particular system. Typically, using a 2½ inch rotor operating at a throughput of about 500 to 1,500 grams of solution per minute requires mixing speeds in the range of from 1,500 to 4,000 RPM to produce membranes with pore ratings in the range of interest.

The liquid nonsolvent system used to dilute the film of casting composition and thereby precipitate the casting resin system, typically by immersion in a bath of the liquid nonsolvent system, can, and preferably does, contain a substantial amount of a solvent for the casting resin system, preferably the one present in the casting solution. That is, the liquid nonsolvent system is comprised of a mixture of a nonsolvent for the casting resin system, e.g., water, and a solvent for the casting resin system, e.g., formic acid. However, on a percentage basis, the amount of solvent present in the liquid nonsolvent system will be less than the amount present in the casting solution. Typically, the liquid nonsolvent system will be comprised of a nonsolvent, e.g., water, present in an amount ranging from about 65 to about 40 weight percent and a solvent for the casting resin system, e.g., formic acid, present in an amount ranging from about 35 to about 60 weight percent. Preferably, the bath of the liquid nonsolvent system is maintained at a substantially constant composition with respect to nonsolvent and solvent by the addition of nonsolvent to the bath, preferably continuously, in a quantity sufficient to compensate for solvent diffusion into the bath from the thin film of casting composition.

Solvents

The solvent, comprising at least part, if not all, of the solvent system in the casting solution of the subject invention can be any solvent for the casting resin system. A preferred solvent is formic acid. Other suitable solvents are other liquid aliphatic acids, such as acetic acid and propionic acid; phenols, such as phenol; the cresols and their halogenated derivatives; inorganic acids, such as hydrochloric, sulfuric and phosphoric; saturated aqueous or alcohol solutions of alcohol-soluble salts, such as calcium chloride, magnesium chloride and lithium chloride; and hydroxylic solvents, including halogenated alcohols.

The only criteria in selecting a solvent are that (1) it form a solution of the polyamide resin and the modifying polymer, (2) it not react chemically with either the polyamide resin or the surface modifying polymer and (3) it be capable of ready removal from the surface modified polyamide membrane. Practical considerations also are important, of course. For example, inorganic acids are more hazardous to work with than are others of the named solvents and corrosion problems must be dealt with. Since formic acid meets the three criteria listed above and is a practical material as well, it is the solvent of choice. Due to economy and ease of handling, water is the nonsolvent of choice for use in the solvent system when a nonsolvent is used in the solvent system. In like manner, the preferred nonsolvent added to the casting solution to induce nucleation thereof is water. The preferred nonsolvent component of the liquid nonsolvent system used to precipitate the casting resin system is also water for the same reasons it is the nonsolvent of choice in the solvent system.

The membrane products of this invention are characterized by being hydrophilic, skinless, microporous and alcohol-insoluble with narrow pore size distributions and pore sizes ranging from about 0.04 to about 10 micrometers; filtration efficiencies from molecular dimensions (pyrogens) up to particulates larger than the pore diameters; film thicknesses in tne range of from about 0.01 to 1.5 millimeters, preferably from about 0.025 to about 0.8 mm; and, in the case of certain of the membranes of this invention, by a negative zeta potential in acidic media including pHs as low as 3. As noted above, the membranes are hydrophilic, that is they are readily wettable by water, in less than 3 seconds, preferably less than 1 second.

The membranes of this invention are further characterized by having surface properties which are substantially controlled by functional polar groups of the modifying polymer which provide the membranes of this invention with the ability to selectively react or interact with (a) particulate matter in a fluid media, (b) dissolved matter in a fluid media, or (c) both (a) and (b). That is, it is believed that the process of this invention provides membranes in which a portion of the functional polar groups of the modifying polymer react or interact with the surface carboxyl and amine end groups of the polyamide membrane to provide intimate bonding of the surface modifying polymer and the polyamide but, because the density of the surface chemical groups or functional polar groups in the surface modifying polymer is relatively high, functional polar groups remain available for reaction or interaction with one or more components of a fluid media. The excess functional polar groups contribute to the desired surface properties of the membrane. Indeed, the modifying polymer in any given membrane is chosen or tailored to fit the desired end use, e.g., a modifying polymer containing carboxyl or sulfonic acid groups may be chosen if a negative zeta potential in acidic media is desired.

The amount of surface modifying polymer and the density of the functional polar groups in the surface modifying polymer are chosen to provide an excess of the functional polar groups, that is, functional polar groups in excess of those reacting or interacting with the end groups of the polyamide. The excess of such groups on the pore surfaces of the membrane are available then as sites for further reaction or interaction. For example, these reactive sites can be used to further modify the membrane with, e.g., bound enzymes. Other alternatives are to use these sites for (1) ion exchange mechanisms or (2) as the basis for dissolved metal entrapment by binding the metal at the reactive site on the membrane surface as a stable complex or coordination compound, (1) and (2) herein defined as "complex formation by interaction".

Surprisingly, the low added levels of the surface modifying polymers produce membranes whose surface characteristics substantially reflect the presence of the functional groups of the surface modifying polymers. Along with their excellent pore structure and, in certain cases, negative zeta potential in acidic media, these membranes have very low levels of extractable matter, making them particularly desirable for use in the filtration of biological and pharmaceutical preparations. Additionally, these membranes can be conveniently and economically prepared by a straightforward, continuous and clean process.

Method Of Testing The Surface Modified Membranes Of the Following Examples

The zeta potential of the membranes of the following examples were evaluated by the methods described below:

Zeta Potential

The zeta potential of membranes of this invention were calculated from measurements of the streaming potential generated by flow of a 0.001 weight percent solution of KCl in distilled water through several layers of the membrane secured in a filter sheet or membrane holder. Zeta potential is a measure of the net immobile electric charge on a membrane surface exposed to a fluid. It is related to the streaming potential generated when the fluid flows through the membrane by the following formula (J. T. Davis et al, *Interfacial Phenomena*, Academic Press, New York, 1963):

$$\text{Zeta Potential} = \frac{4\pi\eta}{D} \cdot \frac{E_s \lambda}{P}$$

where $\eta$ is the viscosity of the flowing solution, D is its dielectric constant, $\lambda$ is its conductivity, $E_s$ is the streaming potential and P is the pressure drop across the membranes during the period of flow. In the following examples, the quantity $4\pi\eta/D$ was constant, having a value $2.052 \times 10^2$, making the zeta potential equal to:

$$\text{Zeta Potential (mV)} = \frac{2.052 \times 10^2 \cdot E_s \text{(volt)} \cdot \lambda \text{(}\mu\text{mho/cm)}}{P\text{(psi)}}$$

General Method For The Preparation Of The Membranes Of Examples 1–5

In the following examples, polyamide membranes were prepared containing a variety of membrane surface modifying polymers using the following general procedure:

Membrane casting solutions were prepared by dissolving nylon 66 resin pellets and the desired surface modifying polymer in a solution of formic acid. The nylon 66 resin used had a viscosity of about 6,000 centipoise when tested at 30 degrees C. in a solution containing about 14.5 parts by weight of nylon 66, about 73 parts by weight formic acid and about 12.5 parts by weight water using a Rion Viscotester with a number 1 rotor (Model VT-04, available from Extech International Corporation, Boston, Massachusetts) operating at 63.8 RPM. Dissolution took place with stirring at about 500 RPM in a jacketed resin kettle maintained at 30 degrees C.. When dissolution was complete (usually within 3 hours), a nonsolvent, water, was added under controlled conditions of concentration, temperature, addition rate and degree of agitation to the casting solution in an amount sufficient to adjust the final concentration of materials to that given in each example and to form a casting composition. The water was pumped in, at the rate specified in each example through an orifice about 1 mm in diameter located under the surface of the solution and about 1 cm above a stirring blade mounted on a vertical shaft, to induce nucleation and form a visible precipitate. Stirring was maintained at about 500 RPM during addition of the water.

The casting composition was filtered through a 10 micrometer filter, after which about 40 grams of casting composition were spread out onto a clean glass plate by means of an adjustable gap doctor blade. The film was then promptly immersed into a bath containing formic acid and water in the amounts given in the examples below.

The membranes were kept immersed in the bath for several minutes to set them. They were then stripped from the glass plate, washed in water to remove residual formic acid and oven-dried for 15 minutes at 96 degrees C. (205 degrees F.) while restrained in a frame to prevent shrinkage. The flat membrane sheets were then used for filter applications or for testing.

EXAMPLE 1

The General Method described above was used to prepare a membrane where the surface modified polymer was Cor-Cat® P-145. The rate of injection of water was about 5 ml/min.. The final casting composition solution contained about 73.7 weight percent formic acid, 9.9 weight percent water, 14.2 weight percent nylon 66 resin and 2.13 weight percent Cor-Cat® P-145. The casting composition was drawn to a thickness of 0.017 inches on a glass plate and immersed in a bath containing 54 weight percent formic acid, the balance water. After the membrane was set, it was processed as described in the General Method until ready for testing.

The membrane produced was wetted completely immediately upon contact with water (in less than 1 second) and had a pore size of 0.8 micrometer as determined by $K_L$ measurement. $K_L$ measurements set forth herein were determined using the technique disclosed in U.S. Pat. No. 4,340,479. The presence of functional groups of the polyethyleneimine at the surface of the membrane was illustrated by the zeta potential of the membrane, which was +10 mV at a pH of 8.0.

EXAMPLE 2

The method of Example 1 was repeated, but with Product #19205-8 (Aldrich Chemical Company) as the surface modifying polymer. The rate of injection of water was about 5 ml/min.. The casting composition consisted of 74.8 weight percent formic acid, 10.1 weight percent water, 14.4 weight percent nylon 66 resin and 0.72 weight percent poly(acrylic acid). The casting composition was drawn to a thickness of 0.021 inches on a glass plate and immersed into a bath containing 50 weight percent formic acid, the balance water. After the membrane was set, it was further processed as described in the General Method until ready for testing.

The membrane produced was wetted completely immediately upon contact with water (in less than 1 second) and had a pore size of 8 micrometers as determined by $K_L$ measurement. The membrane had a zeta potential of −4.0 mV at a pH of 3.6, a pH at which unmodified hydrophilic nylon membrane is strongly positive. This demonstrates that carboxylic acid functional groups of the surface modifying polymer are present at the surface of the membrane and substantially control the surface characteristics thereof, even when the surface modifying polymer is added at this low level.

EXAMPLE 3

The method of Example 1 was repeated, but with Versa ® TL-71 (National Starch Company) as the surface modifying polymer. The rate of injection of water was about 2 ml/min.. The casting composition contained about 74.2 weight percent formic acid, 12.9 weight percent water, 12.1 weight percent nylon 66 resin and 0.62 weight percent Versa ® TL-71. The casting composition was drawn to a thickness of 0.021 inches on a glass plate and immersed in a bath containing 50 weight percent formic acid, the balance water. After the membrane was set, it was further processed as described in the General Method until ready for testing.

The membrane produced was wetted completely upon contact with water (in less than 1 second) and had a pore size of 0.2 micrometers as determined by $K_L$ measurement. The membrane had a zeta potential of −2.4 mV at a pH of 3.6, a pH at which the unmodified nylon membrane is strongly positive, demonstrating that sulfonic acid groups of the modifying polymer are present at the surface of the membrane and substantially control the surface characteristics thereof, even when the surface modifying polymer is added at this low level.

EXAMPLE 4

The method of Example 1 was repeated, but with Gantrez ® 97 (GAF Corporation) as the surface modifying polymer. The rate of injection of water was about 3 ml/min.. The casting composition consisted of about 71.7 weight percent formic acid, 13.8 weight percent water, 13.8 weight percent nylon 66 resin and 0.70 weight percent Gantrez ® S-97. The casting composition was drawn to a thickness of 0.021 inches on a glass plate and immersed in a bath containing 50 weight percent formic acid, the balance water. After the membrane was set it was further processed as described in the General Method until ready for testing.

After drying, the membrane was wetted completely upon contact with water (in less than 1 second). It had a pore size of 0.8 micrometers as determined by $K_L$ measurement and a zeta potential of −8.2 mV at a pH of 3.6, a pH at which unmodified hydrophilic nylon membrane is strongly positive, demonstrating that carboxylic acid functional groups of the Gantrez ® S-97 are present at the surface of the membrane and substantially control the surface characteristics, even at the low levels at which the Gantrez ® S-97 was added.

EXAMPLE 5

The method of Example 1 was repeated, but with Vinol ® 165 (Air Products) as the surface modifying polymer. The rate of water injection was about 5 ml/min.. The casting composition contained about 74.8 weight percent formic acid, 10.1 weight percent water, 14.4 weight percent nylon 66 resin and 0.73 weight percent Vinol ® 165. The casting composition was drawn to a thickness of 0.015 inches on a glass plate and immersed in a bath containing 50 weight percent formic acid, the balance water. After the membrane had set, it was processed further as described in the General Method until ready for testing.

The membrane produced was wetted completely on contact with water (in less than 1 second) and had a pore size of 1.0 micrometer as determined by $K_L$ measurement.

A number of the membranes prepared in the previous examples were tested for the ability to remove metal ions from aqueous solution by complexation with the functional groups of the modifying polymer on the membrane surface. The test was carried out by immersing 16 square centimeters of each membrane in 40 milliliters of a solution of 20 ppm Cu (as copper sulfate pentahydrate in deionized water) for 20 minutes. The copper ion concentration in the solutions, before and after exposure to the membranes, was established by the method described in *Standard Methods of Chemical Analysis*, N. H. Furman, Editor, Volume I, page 408, 6th Edition, Krieger Publishing Company, 1975, using tetramethylethylenediamine as the reagent. For comparative purposes, an unmodified hydrophilic nylon 66 membrane with a 0.2 micrometer pore size was included in the test evaluation. This membrane is listed as Control in Table I and has substantially no functional groups which are available for reaction with the copper ions.

TABLE I

| Membrane of Example | Membrane Surface Functional Groups | Copper Adsorption Capacity in Milligrams per Square Meter Membrane Surface Area |
|---|---|---|
| 1 | amine | 95 |
| 2 | carboxylic acid | 130 |
| 3 | sulfonic acid | 605 |
| 5 | hydroxyl | 167 |
| Control | none | 30 |

The data in Table I demonstrate that the membranes of the present invention, prepared by the addition of certain surface modifying polymers, display surprisingly large metal adsorption capacities. The copper adsorption capacities observed with these membranes is believed to stem from the metal complex forming capability of the functional chemical surface groups in the membranes of the present invention. By contrast, the Control membrane, whose surfaces have not been modified, displays low copper adsorption capacity. The microporous filtration membranes of the present invention have the novel capacity to function as fine filtration membranes with simultaneous removal of metal species from the filtering liquid through complex formation of the membrane surface functional groups with metal species. Such membranes are useful in the recovery of a variety of soluble or dispersed metal catalysts, in the metal detoxification of aqueous fluids and for various other similar applications.

The membrane of Example 1 was tested for its ability to undergo reaction with the dye Cibacron Blue F3G-A. Substrates modified with this dye have been found useful for the reversible binding or immobilization of certain enzymes, albumin, coagulation factors, and interferon (See *Theory and Practice In Affinity Chromatography*, P. V. Sundaram and F. Eckstein, Academic Press, New York, 1978, pages 23–43). The membrane of Example 1 was immersed for 30 minutes at room temperature in a 0.2 weight percent aqueous solution of Cibacron Blue F3G-A (hereinafter referred to as Cibacron Blue), adjusted to a pH of 10 with sodium hydroxide. After exposure to the dye, the membrane was washed by agitation in distilled water until no blue color appeared to be lost in the wash water. The membrane was then dried in an oven for one-half hour at 225 degrees F. (107 degrees C.).

After the above treatment, the membrane of Example 1 had absorbed a substantial quantity of Cibacron Blue, as evidenced by a deep blue membrane color. In order to demonstrate that all of the dye was firmly bound, the membrane was next flushed with distilled water at a volume of 2 liters per square foot of membrane area and then with a similar amount of a 0.01M aqueous solution of tris(hydroxymethyl)aminomethane, adjusted to pH 7.5 with acetic acid (hereinafter referred to as "tris acetate"). This buffer ("tris acetate") and related buffers (e.g., "tris HCl") are commonly used in biochemical preparations and manipulations.

The membrane of Example 1 which had been dyed with Cibacron Blue was next evaluated as a support for affinity chromatography. A membrane suitable for use in affinity chromatography processes where enzymes are employed must firmly bind a substantial amount of enzyme, must retain this bound enzyme during washing with distilled water, and must release the bound enzyme on demand by treating with an appropriate substance, such as a subtrate of the enzyme. To demonstrate such suitability, the dyed membrane of Example 1 was next rinsed with 0.01M tris acetate buffer adjusted to a pH of 7.5 in order to wet the membranes and establish the required pH. The membrane was then treated with the enzyme lactate dehydrogenase (Sigma Chemical Company L2500) by passing a solution containing 2.4 enzyme units/ml in the tris acetate buffer through the membrane at a total volume of 2 liters per square foot of membrane area. The quantity of enzyme bound by the membrane was determined by enzyme assay of aliquots of the enzyme solution before and after passage through the membrane. The amount of enzyme adsorbed to the exposed surfaces of the membrane was calculated by the measured differences in the enzyme concentration in the solution before and after passage through the membrane. Enzyme activity was assayed by observing the enzymatic conversion of NAD (nicotinamide adenine dinucleotide, oxidized form) into NADH (nicotinamide adenine dinucleotide, reduced form) by the standard method described in *Sigma Chemical Company Technical Bulletin UV-200*.

After the membrane was treated with the enzyme, it was flushed with 6 liters of distilled water per square foot of membrane area over a period of about 2 minutes so as to remove any enzyme which had not bound to the membrane. To demonstrate that bound enzyme was not subject to non-specific elution by distilled water, the flushed membrane was immersed in distilled water (about 300 ml per square foot of membrane) for about 10 minutes. The distilled water was then analyzed for the presence of any released enzyme and was found to be substantially free of enzyme activity, demonstrating that the enzyme was tightly bound to the membrane, as required. Biospecific elution of enzyme from the membrane surface was demonstrated by similar challenge with 0.004M NAD in distilled water followed by analysis of the NAD solution for the presence of the eluted enzyme. For comparative purposes, another sample of the surface modified membrane of Example 1 was subjected to the same sequence of treatments except that exposure to Cibacron Blue was omitted. This membrane is designated as Control in Table II.

TABLE II

| Membrane of Example | Quantity of Enzyme Adsorbed in Enzyme Units Per Square Foot | Percent Bound Eluted Non-Specific | Enzyme Specific |
|---|---|---|---|
| 1 | 10,400 | 2% | 43% |
| Control | None | 0 | 0 |

The results obtained with the membrane of Example 1 demonstrate that the membranes of the present invention are useful as supports in affinity chromatography. The surface modified membrane of Example 1 binds high levels of Cibacron Blue chemically without the requirement of prior treatments. The membranes also bind Cibacron Blue in the required state since enzymes are bound in large quantities to the dyed membrane but not to undyed membranes. Moreover, the membrane bound enzyme is not subject to non-specific removal, such as by treatment with water. However, the enzyme is removed specifically in a quantitative manner by the action of an appropriate enzyme substrate as required. Thus, membranes prepared by the novel method of this invention with selected surface modifying polymers having certain functional polar groups are demonstrated to be suitable for applications in affinity chromatography.

The novel surface-modified membranes of this invention are also useful for other biochemical applications. For example, the membrane of Example 1 has unexpected useful properties for the permanent chemical binding of enzymes on the membrane surface. To demonstrate permanent chemical binding of an active enzyme to the membrane surface, the membrane of Example 1 was subjected to chemical treatments designed to allow such permanent chemical immobilization. The reactive chemical groups on the surface of the membrane of Example 1 were reacted with glutaraldehyde as a 25% solution in water by immersion of the membrane for 15 minutes at room temperature. Unbound glutaraldehyde was removed from the membranes by agitating twice for 5 minutes in aqueous solutions of 0.16M sodium chloride.

Next, the chemical immobilization of the enzyme alkaline phosphatase was carried out. The glutaraldehyde-treated membrane was exposed for 15 minutes at room temperature to a solution of the enzyme alkaline phosphatase (Sigma Chemical Company, Product P7640). This solution contained 0.1 mg/ml of total protein dissolved in 0.16M aqueous NaCl and had an enzymatic activity of about 0.4 enzyme units/ml as determined by standard procedures (*Sigma Technical Bulletin* 104). Exposure to the enzyme permitted the membrane surface-bound glutaraldehyde to react with and irreversibly bind the enzyme onto the membrane surface.

Any enzyme which was loosely adsorbed to the membrane but not chemically bound was removed by agitating membranes for three successive 2 minute periods in solutions containing 0.01M tris acetate, buffer at pH 7.5, in 0.16M aqueous NaCl. To ensure complete removal of unreacted enzyme, the membranes were then exhaustively washed with a surfactant solution containing 0.1% Triton X-100 (Rohm and Haas Company, an adduct of nonylphenol with about 10 moles of ethylene oxide) in water. Finally, the surfactant was removed by two successive washes with the tris acetate buffer solution. As a control, a hydrophilic nylon membrane of similar pore size but prepared without the addition of surface-modifying polymer was subjected to the same sequence of treatments in an attempt to similarly immobilize enzyme.

The membrane of Example 1 and the Control were then tested for the presence of active, immobilized enzyme. The presence of membrane-bound enzyme was detected by exposing membranes to a solution of p-nitrophenyl phosphate, a substrate for the enzyme, and observing the characteristic change in the color of the solution caused by the reaction of the substrate with the enzyme. Thus, a 10×10 mm piece of each membrane was exposed for approximately one-half hour to a 5 ml aliquot of solution containing 0.001M p-nitrophenyl phosphate in 0.1M aqueous "tris" buffer adjusted to pH 9 with HCl. The presence of membrane surface-bound enzyme activity was easily detected by the formation of a brilliant yellow color due to the action of the enzyme on the substrate. The level of enzyme activity was measured by visual color comparison with standard solutions containing known concentrations of the dissolved enzyme. As shown by the data in Table III, the membrane of Example 1 shows a high level of enzyme activity, indicating the chemical binding of enzyme by the functional groups of the surface-modified membrane of this invention. In contrast, the Control membrane prepared without added membrane surface-modifying polymer did not chemically bind enzyme as shown by the complete absence of enzyme activity.

TABLE III

| Membrane of Example | Measured Enzyme Activity in Enzyme Units Per Square Foot Membrane Area |
|---|---|
| 1 | 25 |
| Control | less than 0.1 |

These results illustrate several important and surprising points. First, it is demonstrated that the surface-modified membranes of the present invention can be used as supports for the chemical immobilization of enzyme. The results clearly demonstrate that enzymes can be permanently attached to the membrane surface in large quantities. Moreover, the immobilized enzyme has been demonstrated to be permanently bound to the membrane surface and yet to retain high enzymatic activity. Furthermore, the method of immobilization described above will be recognized by those skilled in the art as (1) exposing the enzyme to only a very mild or benign treatment and (2) providing a very simple, clean and fast process requiring no prior membrane surface preparation.

Membranes of this invention are useful then as supports in affinity chromatography processes where a solute is contacted with the support, particularly in such processes where an enzyme is bound to the membrane surface.

Industrial Applicability

The surface modified membranes of the present invention have been demonstrated to be superior in many important filtration related properties to prior art membranes. They can be used for filtering applications in their manufactured form, with or without the incorporation of the substrate upon which they are formed. Two or more membranes can be combined or secured to each other to form multiple layer membrane filter sheets or they may be converted into filter elements by known methods and employed in filter cartridges, e.g., as filter elements in the form of a corrugated sheet supported within a conventional cartridge.

Certain of the membranes of this invention display negative zeta potentials in acidic media including at a pH as low as 3. Accordingly, these membranes show greatly enhanced removal efficiencies toward positively charged particles in acidic media. Furthermore, they have enhanced efficiency to selectively remove particulate matter from fluid media, to remove undesired dissolved material from fluid media, to concentrate desirable dissolved material, to be chemically modified as required to be useful for processing biological and biochemical preparations and they can serve as substrates for the immobilization of enzymes.

These membranes have uses in industry, particularly in the pharmaceutical, medical and biochemical fields, for treatment of various fluid media. These include treatment of waste streams for the recovery of valuable metals, the immobilization of enzymes, and generally for any use where an ion containing fluid must be filtered to a high degree of clarity.

We claim:

1. A process for preparing a surface modified, skinless, hydrophilic, microporous, alcohol-insoluble polyamide membrane with controlled pore surface properties, capable of reacting or interacting in a controlled manner with (a) particulate matter in a fluid, (b) nonparticulate matter in a fluid, or (c) both (a) and (b) and that is readily wetted by water, which comprises:

(1) preparing a casting solution comprised of (A) a casting resin system comprised of (a) an alcohol-insoluble polyamide resin having a ratio $CH_2$:NHCO of methylene $CH_2$ to amide NHCO groups within the range of from about 5:1 to about 7:1, and (b) a water-soluble, membrane surface modifying polymer having functional polar groups selected from the group consisting of hydroxyl, carboxyl, and amino or a non-reacting combination thereof, and a molecular weight of 20,000 or greater, and (B) a solvent system in which said casting resin system is soluble;

(2) inducing nucleation of said casting solution by controlled addition of nonsolvent for said casting resin system under controlled conditions of concentration, temperature, addition rate and degree of agitation to obtain a visible precipitate of casting resin system particles, thereby forming a casting composition;

(3) spreading said casting composition on a substrate to form a thin film thereof on the substrate;

(4) contacting and diluting the film of said casting composition with a liquid nonsolvent system for said casting resin system comprised of a mixture of solvent and nonsolvent liquids, thereby precipitating said casting resin system from said casting composition in the form of a thin, skinless, hydrophilic, surface modified, microporous, polyamide membrane with controlled surface properties;

(5) washing said membrane to remove solvent; and (6) drying said membrane.

2. The process of claim 1 in which precipitated casting resin system particles are redissolved before spreading said casting compositions on said substrate.

3. The process of claim 1 in which precipitated casting resin system particles are filtered out before spreading said casting composition on said substrate.

4. The process of claim 1 in which said polyamide resin is polyhexamethylene adipamide.

5. The process of claim 1 in which said polyamide resin is poly-e-caprolactam.

6. The process of claim 1 in which said polyamide resin is polyhexamethylene sebacamide.

7. The process of claim 1 in which said polyamide resin is polyhexamethylene adipamide, said solvent system for said casting resin system comprises formic acid, and said nonsolvent added to induce nucleation is water.

8. The process of claim 7 wherein said solvent system for said casting resin system comprises formic acid and water.

9. The process of claim 1 in which the film of casting composition is contacted with said liquid nonsolvent system by immersing said film carried on said substrate in a bath of said liquid nonsolvent system.

10. The process of claim 1 wherein said polyamide resin is present in said casting solution in an amount of from about 10% to 20%, said membrane surface modifying polymer is present in an amount of from about 0.5% to 3.0%, said solvent system comprises formic acid and water and wherein said formic acid is present in said casting solution in an amount of from about 60% to 80%, and said water is present in said casting solution in an amount of from 0% to about 30%, all percentages based on the weight of all the components in said casting solution.

11. The process of claim 1 wherein said membrane surface modifying polymer has a molecular weight of from about 25,000 to about 150,000.

12. The process of claim 1 wherein the surfaces of said membrane have the ability to undergo reaction by reaction of functional polar groups on said surfaces.

13. The process of claim 1 wherein said functional group comprises hydroxyl and said membrane surface modifying polymer comprises polyvinyl alcohol.

14. The process of claim 1 wherein said functional group comprises carboxyl and said membrane surface modifying polymer comprises polyacrylic acid.

15. The process of claim 1 wherein said functional group comprises amino and said membrane surface modifying polymer is selected from the group consisting of amino styrene, amino alkyl acrylates and polyethyleneimines.

16. The process of claim 1 in which said membrane surface modifying polymer is selected from the class consisting of polyacrylic acid, a fully hydrolyzed copolymer of maleic anhydride with methyl vinyl ether, a homopolymer of aziridine with a molecular weight of 30,000 or greater and polyvinyl alcohol.

17. The process of claim 1 in which part of the precipitated casting resin particles are redissolved and part are filtered out before spreading said casting composition on said substrate.

18. The process of claim 1 in which said casting composition is continuously spread onto said substrate, said thin film of said casting composition is continuously immersed in a bath of said liquid nonsolvent system, and the bath is maintained at a substantially constant composition with respect to nonsolvent and solvent by the addition of nonsolvent to the bath in a quantity sufficient to compensate for solvent diffusion into the bath from said thin film of said casting composition.

19. The process of claim 18 in which the substrate is a porous web having an open structure which is wetted and impregnated by the casting composition, thereby forming a membrane film having the porous web incorporated as a part thereof.

20. The process of claim 19 in which the substrate is a porous, fibrous polyester sheet.

21. The process of claim 1 in which said membrane is stripped from said substrate after washing and before drying.

22. A process for preparing a surface modified, skinless, hydrophilic, microporous, alcohol-insoluble polyhexamethylene adipamide resin membrane with controlled pore surface properties, capable of reacting or interacting in a controlled manner with (a) particulate matter in a fluid, (b) non-particulate matter in a fluid, or (c) both (a) and (b) and that is readily wetted by water, which comprises:

(1) preparing a casting solution comprised of (A) a casting resin system comprised of (a) an alcohol-insoluble polyhexamethylene adipamide resin in a concentration within the range from about 10% to about 20% by weight and (b) a water-soluble, membrane surface modifying polymer having functional polar groups selected from the group consisting of hydroxyl, carboxyl, and amino or a non-reacting combination thereof, and a molecular weight of from about 25,000 to about 150,000 in a concentration within the range of from about 0.5% to about 3% and (B) a solvent system comprised of (a) formic acid in a concentration of from about 60% to about 80% and (b) from 0% to about 30% water, all percentages based on the weight of all the components in said casting solution;

(2) inducing nucleation of said casting solution by adding water thereto while controlling temperature, rate of addition of water and degree of agitation to obtain a visible precipitate of casting resin system particles, thereby forming a casting composition;

(3) spreading said casting composition on a substrate to form a thin film of said casting composition thereon;

(4) contacting and diluting said thin film of said casting composition with an aqueous solution containing from about 35% to about 60% formic acid, thereby precipitating said casting resin system from said casting composition as a thin, surface modified, skinless, hydrophilic, microporous, polyamide membrane;

(5) washing said membrane to remove formic acid; and (6) drying said membrane.

23. The process of claim 22 in which said membrane is stripped from said substrate after washing and before drying.

24. The process of claim 22 in which at least a portion of said visible precipitate of casting resin system particles is redissolved before spreading said casting composition on said substrate.

25. The process of claim 22 in which said visible precipitate of casting resin system particles is filtered out before spreading said casting composition on said substrate.

26. A surface modified, skinless, hydrophilic, microporous, alcohol-insoluble polyamide membrane derived from an alcohol-insoluble hydrophobic polyamide resin having a ratio $CH_2$:NHCO of methylene $CH_2$ to amide NHCO groups within the range of from about 5:1 to about 7:1, said membrane having an integral microstructure and characterized by (1) the surface properties thereof being substantially controlled by functional polar groups of a membrane surface modifying polymer having a molecular weight of 20,000 or greater, said functional polar groups selected from the group consisting of hydroxyl, carboxyl, and amino, or a non-reacting combination thereof, (2) said membrane surface modifying polymer being homogeneously distributed in said membrane, and (3) having the capability of reacting or interacting in a controlled manner with (a) particulate matter in a fluid, (b) non-particulate matter in a fluid, or (c) both (a) and (b).

27. The microporous, alcohol-insoluble polyamide membrane of claim 26 wherein said membrane has a negative zeta potential in acidic media.

28. The microporous, alcohol-insoluble polyamide membrane of claim 27 wherein said surface modifying polymer has carboxyl functional polar groups.

29. The microporous, alcohol-insoluble polyamide membrane of claim 26 wherein the surfaces of said membrane have the ability to undergo complex formation by interaction of functional polar groups on said surfaces with metallic species in a fluid media.

30. The membrane of claim 29 wherein said complex formation is ionic interaction.

31. The membrane of claim 29 wherein said complex formation is the formation of stable metal complexes.

32. The membrane of claim 29 wherein said functional polar group comprises amino.

33. The microporous, alcohol-insoluble polyamide membrane of claim 26 wherein the surfaces of said membrane have the ability to undergo reaction by reaction of functional polar groups on said surfaces.

34. The membrane of claim 33 wherein said reaction is the immobilization of enzymes.

35. The membrane of claim 33 wherein said functional polar groups are selected from the class consisting of hydroxyl, carboxyl and amino.

36. The membrane of claim 26 wherein said functional group comprises hydroxyl and said membrane surface modifying polymer comprises polyvinyl alcohol.

37. The membrane of claim 26 wherein said functional group comprises carboxyl and said membrane surface modifying polymer comprises polyacrylic acid.

38. The membrane of claim 26 wherein said functional group comprises amino and said membrane surface modifying polymer is selected from the group consisting of amino styrene, amino alkyl acrylates and polyethyleneimines.

39. The membrane of claim 26 wherein said membrane surface modifying polymer has a molecular weight of from about 25,000 to about 150,000.

40. The microporous, alcohol-insoluble polyamide membrane of claim 26 having pore ratings of 0.04 micrometer to 10 micrometers.

41. The microporous, alcohol-insoluble polyamide membrane of claim 26 having pore ratings of 0.1 micrometer to 5 micrometers.

42. The microporous, alcohol-insoluble polyamide membrane of claim 26 in which said polyamide resin is polyhexamethylene adipamide.

43. The microporous, alcohol-insoluble polyamide membrane of claim 26 comprising two of said membranes secured to each other and forming a multiple layer membrane filter sheet.

44. The microporous, alcohol-insoluble polyamide membrane of claim 26 having a thickness within the range of from about 0.01 to about 1.5 mm.

45. The microporous, alcohol-insoluble polyamide membrane of claim 26 having a thickness within the range of from about 0.025 to about 0.8 mm.

46. A filter element comprised of the surface modified, skinless, hydrophilic, microporous, alcohol-insoluble polyamide membrane of claim 26.

47. The filter element of claim 46 in which said membrane is in the form of a corrugated sheet.

48. A method for the removal of metal species from a fluid medium by complex formation comprising contacting said medium with the microporous, alcohol-insoluble, polyamide membrane of claim 26.

49. The method of claim 48 wherein said complex formation is ion exchange.

50. The method of claim 40 wherein said complex formation is the formation of stable metal complexes.

51. A method for immobilizing an enzyme comprising contacting said enzyme with the microporous, alcohol-insoluble polyamide membrane of claim 26.

52. The microporous, alcohol insoluble polyamide membrane of claim 26 further characterized by having an enzyme bound to the surfaces thereof.

53. In the practice of affinity chromatography wherein a solute is contacted with an affinity chromatography support, the improvement wherein said support comprises the polyamide membrane of claim 52.

54. In the practice of affinity chromatography wherein a solute is contacted with an affinity chromatography support, the improvement wherein said support comprises the polyamide membrane of claim 26.

55. An integral surface modified, skinless, hydrophilic, microporous, alcohol-insoluble polyamide membrane derived from about 80 to about 99.9% of an alcohol-insoluble hydrophobic polyamide resin having a ratio $CH_2$:NHCO of methylene $CH_2$ to amide NHCO groups within the range of from about 5:1 to about 7:1 and from about 20 to about 0.1% of a membrane surface modifying polymer having functional polar groups, said functional polar groups selected from the group consisting of hydroxyl, carboxyl, and amino, or a nonreacting combination thereof, and a molecular weight of 20,000 or greater, said membrane having an integral microstructure and characterized by (1) the surface properties thereof being substantially controlled by functional polar groups of the membrane surface modifying polymer, (2) said membrane surface modifying polymer being homogeneously distributed in said membrane, and (3) having the capability of reacting or interacting in a controlled manner with (a) particulate matter in a fluid, (b) non-particulate matter in a fluid, or (c) both (a) and (b).

56. The membrane of claim 55 wherein said membrane surface modifying polymer has a molecular weight of from about 25,000 to about 150,000.

57. The microporous, alcohol-insoluble polyamide membrane of claim 55 wherein the surfaces of said membrane have the ability to undergo reaction by reaction of functional polar groups on said surfaces.

58. The membrane of claim 55 wherein said functional group comprises hydroxyl and said membrane surface modifying polymer comprises polyvinyl alcohol.

59. The membrane of claim 55 wherein said functional group comprises carboxyl and said membrane surface modifying polymer comprises polyacrylic acid.

60. The membrane of claim 55 wherein said functional group comprises amino and said membrane surface modifying polymer is selected from the group consisting of amino styrene, amino alkyl acrylates and polyethyleneimines.

61. The membrane of claim 55 wherein said modifying polymer is present in said membrane in an amount of from about 1 to about 5%.

62. The membrane of claim 55 wherein said modifying polymer is present in said membrane in an amount of from about 1 to about 2%.

63. A surface modified, skinless, hydrophilic, microporous, alcohol-insoluble polyamide membrane derived from an alcohol-insoluble hydrophobic polyamide resin having a ratio $CH_2:NHCO$ of methylene $CH_2$ to amide NHCO groups within the range of from about 5:1 to about 7:1, said membrane having an integral microstructure and characterized by (1) the surface properties thereof being substantially controlled by functional polar groups of a membrane surface modifying polymer having a molecular weight of 20,000 or greater, said functional polar groups comprising hydroxyl, (2) said membrane surface modifying polymer being homogeneously distributed in said membrane, and (3) having the capability of reacting or interacting in a controlled manner with (a) particulate matter in a fluid, (b) non-particulate matter in a fluid, or (c) both (a) and (b).

64. A surface modified, skinless, hydrophilic, microporous, alcohol-insoluble polyamide membrane derived from an alcohol-insoluble hydrophobic polyamide resin having a ratio $CH_2:NHCO$ of methylene $CH_2$ to amide NHCO groups within the range of from about 5:1 to about 7:1, said membrane having an integral microstructure and characterized by (1) the surface properties thereof being substantially controlled by functional polar groups of a membrane surface modifying polymer having a molecular weight of 20,000 or greater, said functional polar groups comprising carboxyl, (2) said membrane surface modifying polymer being homogeneously distributed in said membrane, and (3) having the capability of reacting or interacting in a controlled manner with (a) particulate matter in a fluid, (b) non-particulate matter in a fluid, or (c) both (a) and (b).

65. A surface modified, skinless, hydrophilic, microporous, alcohol-insoluble polyamide membrane derived from an alcohol-insoluble hydrophobic polyamide resin having a ratio $CH_2:NHCO$ of methylene $CH_2$ to amide NHCO groups within the range of from about 5:1 to about 7:1, said membrane having an integral microstructure and characterized by (1) the surface properties thereof being substantially controlled by functional polar groups of a membrane surface modifying polymer having a molecular weight of 20,000 or greater, said functional polar groups comprising amino, (2) said membrane surface modifying polymer being homogeneously distributed in said membrane, and (3) having the capability of reacting or interacting in a controlled manner with (a) particulate matter in a fluid, (b) non-particulate matter in a fluid, or (c) both (a) and (b).

* * * * *